US009296922B2

(12) United States Patent
Yao et al.

(10) Patent No.: US 9,296,922 B2
(45) Date of Patent: Mar. 29, 2016

(54) STABLE METAL COMPOUNDS AS HARDMASKS AND FILLING MATERIALS, THEIR COMPOSITIONS AND METHODS OF USE

(71) Applicants: Huirong Yao, Plainsboro, NJ (US); Salem K. Mullen, Florham Park, NJ (US); Elizabeth Wolfer, Bethlehem, PA (US); Douglas McKenzie, Easton, PA (US); JoonYeon Cho, Bridgewater, NJ (US); Munirathna Padmanaban, Bridgewater, NJ (US)

(72) Inventors: Huirong Yao, Plainsboro, NJ (US); Salem K. Mullen, Florham Park, NJ (US); Elizabeth Wolfer, Bethlehem, PA (US); Douglas McKenzie, Easton, PA (US); JoonYeon Cho, Bridgewater, NJ (US); Munirathna Padmanaban, Bridgewater, NJ (US)

(73) Assignee: AZ ELECTRONIC MATERIALS (LUXEMBOURG) S.A.R.L., Luxembourg (LU)

( * ) Notice: Subject to any disclaimer, the term of this patent is extended or adjusted under 35 U.S.C. 154(b) by 187 days.

(21) Appl. No.: 14/015,222

(22) Filed: Aug. 30, 2013

(65) Prior Publication Data
US 2015/0064904 A1 Mar. 5, 2015

(51) Int. Cl.
| | |
|---|---|
| C07F 7/08 | (2006.01) |
| G03F 7/075 | (2006.01) |
| C09D 185/00 | (2006.01) |
| H01L 21/033 | (2006.01) |
| C08G 77/58 | (2006.01) |
| G03F 7/09 | (2006.01) |

(52) U.S. Cl.
CPC .............. *C09D 185/00* (2013.01); *C07F 7/08* (2013.01); *C08G 77/58* (2013.01); *G03F 7/0752* (2013.01); *G03F 7/091* (2013.01); *G03F 7/094* (2013.01); *H01L 21/0332* (2013.01); *H01L 21/0337* (2013.01); *H01L 21/0338* (2013.01)

(58) Field of Classification Search
CPC ....... G03F 7/0752; G03F 7/091; G03F 7/094; C09D 185/00; C08G 77/58; C08G 79/00; H01L 21/0332; H01L 21/0337; H01L 21/0338; C07F 7/08
USPC ............ 438/694; 524/262; 556/1, 10, 12, 51, 556/42; 430/270.1, 272.1, 322, 325, 329, 430/330, 331
See application file for complete search history.

(56) References Cited

U.S. PATENT DOCUMENTS

| | | | | |
|---|---|---|---|---|
| 3,035,071 A | * | 5/1962 | Haslam | C07F 7/0836 528/29 |
| 3,474,054 A | | 10/1969 | White | |
| 3,625,934 A | * | 12/1971 | Rinse | 528/30 |
| 3,758,269 A | * | 9/1973 | Bartsch et al. | D06M 15/41 8/531 |
| 4,200,729 A | | 4/1980 | Calbo | |
| 4,251,665 A | | 2/1981 | Calbo | |
| 4,347,347 A | * | 8/1982 | Yajima | C01B 31/301 528/10 |
| 4,361,691 A | * | 11/1982 | Yajima | C08G 77/54 525/475 |
| 4,416,789 A | * | 11/1983 | Shidlovsky | C10M 169/04 346/137 |
| 4,455,414 A | * | 6/1984 | Yajima | C01B 31/301 528/10 |
| 4,491,628 A | | 1/1985 | Ito et al. | |
| 4,529,766 A | * | 7/1985 | Starmer | C08K 5/11 524/310 |
| 5,178,989 A | * | 1/1993 | Heller | G03F 7/0042 216/48 |

(Continued)

FOREIGN PATENT DOCUMENTS

| | | |
|---|---|---|
| EP | 2 447 775 A1 | 5/2012 |
| JP | 63-56529 A | 3/1988 |

(Continued)

OTHER PUBLICATIONS

Machine translation of JP 2009-173910 A (no date).*

(Continued)

*Primary Examiner* — Amanda C Walke
(74) *Attorney, Agent, or Firm* — Mitchell Brustein

(57) ABSTRACT

The present invention relates to novel, soluble, multi-ligand-substituted metal oxide compounds to form metal oxide films with improved stability as well as compositions made from them and methods of their use. Specifically, the invention pertains to compounds having the following structure (I) wherein M is a metal and n is 1 to 20, and wherein at least one of $R_1, R_2, R_3$, and $R_4$ is i) and at least at least one of $R_1, R_2, R_3$, and $R_4$ is ii), where i) is a silicon bearing organic moiety having at least 2 carbons, and ii) is an organic moiety. The invention also relates to spin-coatable compositions of compounds of structure (I) dissolved into a solvent. The present invention further relates to processes using this spin coatable composition to form a coating on a patterned substrate.

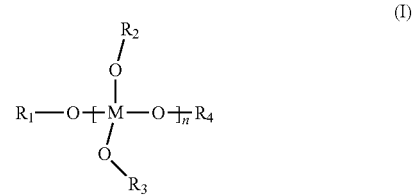

(I)

19 Claims, No Drawings

(56) References Cited

U.S. PATENT DOCUMENTS

| | | | |
|---|---|---|---|
| 5,187,019 A | 2/1993 | Calbo et al. | |
| 5,350,660 A | 9/1994 | Urano et al. | |
| 5,548,050 A * | 8/1996 | Kushibiki | C08G 79/00 528/10 |
| 5,563,228 A * | 10/1996 | Ogawa | C08G 79/00 528/10 |
| 5,772,978 A | 6/1998 | Bailey et al. | |
| 5,843,624 A | 12/1998 | Houlihan et al. | |
| 5,879,859 A | 3/1999 | Buchwalter et al. | |
| 6,242,156 B1 | 6/2001 | Teng | |
| 6,348,299 B1 | 2/2002 | Aviram et al. | |
| 6,447,980 B1 | 9/2002 | Rahman et al. | |
| 6,723,488 B2 | 4/2004 | Kudo et al. | |
| 6,790,587 B1 | 9/2004 | Feiring et al. | |
| 6,818,258 B2 | 11/2004 | Kaneko et al. | |
| 6,849,377 B2 | 2/2005 | Feiring et al. | |
| 6,866,984 B2 | 3/2005 | Jung et al. | |
| 6,916,590 B2 | 7/2005 | Kaneko et al. | |
| 7,416,834 B2 | 8/2008 | Abdallah et al. | |
| 7,560,580 B2 * | 7/2009 | Shin | C08G 77/58 556/10 |
| 7,727,902 B2 | 6/2010 | Takei et al. | |
| 7,767,368 B2 | 8/2010 | Fukushima et al. | |
| 7,799,396 B2 * | 9/2010 | Uehara | B32B 27/30 427/337 |
| 7,803,458 B2 | 9/2010 | Flaim et al. | |
| 8,039,201 B2 | 10/2011 | Yao et al. | |
| 8,343,691 B2 * | 1/2013 | Mizushima | G03F 7/001 359/3 |
| 8,367,771 B2 * | 2/2013 | Shin | C08G 77/58 525/100 |
| 8,568,958 B2 | 10/2013 | Yao et al. | |
| 2003/0235786 A1 | 12/2003 | Krishnamurthy et al. | |
| 2004/0029041 A1 | 2/2004 | Shih et al. | |
| 2004/0058275 A1 | 3/2004 | Neef et al. | |
| 2004/0102048 A1 | 5/2004 | Yamaguchi | |
| 2004/0181031 A1 | 9/2004 | Nogi et al. | |
| 2004/0224616 A1 | 11/2004 | Shiho et al. | |
| 2005/0164133 A1 | 7/2005 | Rangarajan et al. | |
| 2006/0263708 A1 | 11/2006 | Wu et al. | |
| 2007/0015083 A1 | 1/2007 | Babidh et al. | |
| 2007/0116640 A1 | 5/2007 | Kim et al. | |
| 2007/0134916 A1 | 6/2007 | Iwabuchi et al. | |
| 2007/0224483 A1 * | 9/2007 | Alberti | C01B 25/372 429/494 |
| 2007/0243473 A1 | 10/2007 | Mizushima et al. | |
| 2007/0260025 A1 * | 11/2007 | Elder | C07D 333/54 526/126 |
| 2008/0044764 A1 | 2/2008 | Takahashi et al. | |
| 2008/0076064 A1 | 3/2008 | Sun | |
| 2009/0239080 A1 | 9/2009 | Ito et al. | |
| 2009/0286188 A1 | 11/2009 | Hatakeyama et al. | |
| 2010/0028804 A1 | 2/2010 | Iwato et al. | |
| 2010/0099044 A1 | 4/2010 | Hatakeyama et al. | |
| 2010/0130697 A1 | 5/2010 | Katayama et al. | |
| 2011/0081615 A1 | 4/2011 | Kon | |
| 2011/0207864 A1 | 8/2011 | Nakamura et al. | |
| 2012/0178261 A1 | 7/2012 | Kanno et al. | |
| 2012/0223418 A1 | 9/2012 | Stowers et al. | |
| 2012/0264039 A1 | 10/2012 | Ito et al. | |
| 2012/0288300 A1 | 11/2012 | Matsusaki et al. | |
| 2012/0323008 A1 * | 12/2012 | Barry | C23C 16/18 546/11 |
| 2012/0328990 A1 * | 12/2012 | Yao | C08K 5/0091 430/311 |
| 2013/0040140 A1 | 2/2013 | Joo et al. | |
| 2013/0123137 A1 | 5/2013 | Reichardt et al. | |
| 2014/0000948 A1 | 1/2014 | Nagai et al. | |
| 2014/0159278 A1 * | 6/2014 | Yao | C07F 7/28 264/212 |
| 2014/0273447 A1 * | 9/2014 | Ogihara | G03F 7/0752 438/671 |
| 2014/0356792 A1 | 12/2014 | Noya | |
| 2015/0004801 A1 * | 1/2015 | Rahman | G03F 7/091 438/763 |
| 2015/0024522 A1 * | 1/2015 | Wang | C08J 7/00 438/26 |

FOREIGN PATENT DOCUMENTS

| | | | |
|---|---|---|---|
| JP | 3-138922 A | 6/1991 | |
| JP | 6-32756 A | 2/1994 | |
| JP | 2000-10293 A | 1/2000 | |
| JP | 2005-307101 A | 11/2005 | |
| JP | 2006-98284 A | 4/2006 | |
| JP | 2007-61720 A | 3/2007 | |
| JP | 2009-173910 A * | 8/2009 | C08G 79/00 |

OTHER PUBLICATIONS

Form PCT/ISA/220, Form PCT/ISA/210, and Form PCT/ISA/237 dated Aug. 11, 2014 for PCT/EP2014/063593 which corresponds to U.S. Appl. No. 13/930,711.

Notification of the First Office Action dated Sep. 1, 2014 from the Chinese Patent Office for CN2012800262639, which corresponds to U.S. Appl. No. 13/164,869.

English Translation of Notification of the First Office Action dated Sep. 1, 2014 from the Chinese Patent Office for CN2012800262639, which corresponds to U.S. Appl. No. 13/164,869.

Form PCT/ISA/220, Form PCT/ISA/210, and Form PCT/ISA/237 for PCT/EP2013/075815 dated Nov. 28, 2014 for PCT/EP2014/067749, which corresponds to U.S. Appl. No. 14/015,222.

Office Action notification date Mar. 11, 2015 for U.S. Appl. No. 14/237,720.

Form PCT/ISA/220, Form PCT/ISA/210, and Form PCT/ISA/237 dated Feb. 6, 2015 for PCT/EP2014/076919, which corresponds to U.S. Appl. No. 14/015,222.

Office Action notification date Mar. 31, 2015 for U.S. Appl. No. 13/930,711.

Restriction Requirement notification date Mar. 12, 2015 for U.S. Appl. No. 13/707,993.

Notice of Allowance and Fee(s) Due notification date Jun. 24, 2015 for U.S. Appl. No. 14/237,720.

Office Action notification date Jul. 10, 2015 for U.S. Appl. No. 14/154,929.

Satterfield, C. W., Heterogeneous Catalysis in Industrial Practice, 2nd Edition, McGraw-Hill, Inc., New York, Chapter 1, pp. 1-pp. 30 (1991.

International Search Report for PCT/JP2012/070426 date of mailing Sep. 4, 2012, which corresponds to U.S. Appl. No. 14/237,720.

Form PCT/ISA/220, Form PCT/ISA/210, and Form PCT/ISA/237 for PCT/IB2012/001219 dated Oct. 19, 2012, which corresponds to U.S. Appl. No. 13/164,869.

Form PCT/IB/326, Form PCT/IB/373, and Form PCT/ISA/237 for PCT/IB2012/001219 dated Jan. 9, 2014, which corresponds to U.S. Appl. No. 13/164,869.

Machine Language English Abstract from JPO of 3-138922 A.

Machine Language English Abstract from JPO of JP 63-56529 A.

"Alkylenes", PAC, 1995, 67, 1307, (Glossary of class names of organice compounds and reactivity intermediates based on structure (IUPAC Recommendations 1995) on p. 1314, obtained from hhttp://goldbook.iupac.org/!00227-plain.html on Mar. 11, 2013.

D. Abdallah et al., "Image Reversal Trilayer Process Using Standard Positive Photoresist", SPIE vol. 7273, No. 72732K, pp. 72732K-1-pp. 72732K-9 (2009).

D. Bajuk-Bogdanovic, "A Study of 12-tungstosilicic acid and 12-molybdophosphoric acids in solution," Journal of the Serbian Chemical Society vol. 73(2), pp. 197-pp. 209 (2008).

H. Levy et al., "Structure of-Silico—Tungstic acid in Aqueous solution", The Journal of Chemical Physics vol. 30 No. 6, pp. 1486-pp. 1959.

J. Meador et al., "193-nm Multilayer Imaging Systems", SPIE vol. 5039, pp. 948-pp. 959 (2003).

J. Meador et al., "New Materials for 193-nm Trilayer Imaging", SPIE vol. 5376, pp. 1136-pp. 1148 (2004).

(56) References Cited

OTHER PUBLICATIONS

S. Moon et al., Three-Component Photopolymers Based on Thermal Cross-Linking and Acidolytic De-Cross-Linking of Vinyl Ether Groups. Effects of Binder Polymers on Photopolymer Characterictics, Chem. Mater. vol. 6, pp. 1854-pp. 1880 (1994).

M. Pope et al., "Polyoxymetalate Chemistry: An Old Field with New Dimensions in Several Disciplines", Angew. Chem. Int. Ed. Engl. vol. 30, pp. 34-pp. 48 (1991).

H. Schacht et al., "Acid Labile Cross-Liked Units: A Concept for Improved Positive Deep-UV Photoresists", ACS Symp. Ser. 706, pp. 78-pp. 94 (1998).

A. Scroggie et al., "The Crystal Structure of Anhydrous Silicotungstic Acid and Related Compounds, and Their Probable Molecular Formulas," Proceedings of the National Academy of Sciences vol. 15, No. 1, pp. 1-pp. 8 (1929).

Yamaoka et al., "Reactions of vinyl ethers and application to photoreactive process", Trends in Photochemistry and. Photobiology vol. 7, pp. 45-pp. 70 (2001).

Form PCT/ISA/220, Form PCT/ISA/210, and Form PCT/ISA/237 for PPCT/EP2013/075815 dated Jul. 9, 2014 which corresponds to U.S. Appl. No. 13/707,993.

Baxendale et al., "The Reduction of Molybdenum(II) Trifluoroacetate by Pulse Radiolysis in Methanols", Journal of the American Chemical Society vol. 98 No. 2, pp. 637-pp. 638 (1976).

Burch et al., "Scrambling of Fluoro-, Methoxyl, Dimethylamino-, and Methyl Gropus with Chlorine Atoms of Methoxyl with Dimethylaminol-Groups on Germanium", J. Chm. Soc. (A), pp. 586-pp. 589 (1966).

Sartori et al., "Uber die Darstellung und Eigenschaften von Perflouracyloxy-Verbindungen der vierten Gruppe des Periodensystems", Chem. Ber. vol. 100 No. 6, pp. 2049-pp. 2063 (1967).

* cited by examiner

STABLE METAL COMPOUNDS AS HARDMASKS AND FILLING MATERIALS, THEIR COMPOSITIONS AND METHODS OF USE

FIELD OF INVENTION

The present invention relates to novel soluble, multi-ligand-substituted metal compounds with improved stability and novel compositions comprising the metal compounds, which are useful as metal hard masks with good trench or via filling properties in forming microlithographic features, and with good plasma etch resistance in oxygen based plasmas. The novel compositions are used in processes for forming fine patterns on semiconductor substrates.

BACKGROUND

Metal oxide films are useful in a variety of applications in the semiconductor industry such as, for example, lithographic hardmasks, underlayers for anti-reflective coatings and electro-optical devices.

Photoresist compositions are used in microlithography processes for making miniaturized electronic components such as in the fabrication of computer chips and integrated circuits. Generally, a thin coating of a photoresist composition is applied to a substrate, such as a silicon based wafer used for making integrated circuits. The coated substrate is then baked to remove a desired amount of solvent from the photoresist. The baked coated surface of the substrate is then image-wise exposed to actinic radiation, such as, visible, ultraviolet, extreme ultraviolet, electron beam, particle beam and X-ray radiation.

The radiation causes a chemical transformation in the exposed areas of the photoresist. The exposed coating is treated with a developer solution to dissolve and remove either the radiation-exposed or the unexposed areas of the photoresist.

The trend towards the miniaturization of semiconductor devices has led to the use of new photoresists that are sensitive to shorter and shorter wavelengths of radiation and has also led to the use of sophisticated multilevel systems to overcome difficulties associated with such miniaturization.

Absorbing antireflective coatings and underlayers in photolithography are used to diminish problems that result from radiation that reflects from substrates which often are highly reflective. Reflected radiation results in thin film interference effects and reflective notching. Thin film interference, or standing waves, result in changes in critical line width dimensions caused by variations in the total light intensity in the photoresist film as the thickness of the photoresist changes. Interference of reflected and incident exposure radiation can cause standing wave effects that distort the uniformity of the radiation through the thickness. Reflective notching becomes severe as the photoresist is patterned over reflective substrates containing topographical features, which scatter light through the photoresist film, leading to line width variations, and in the extreme case, forming regions with complete loss desired dimensions. An antireflective coating film coated beneath a photoresist and above a reflective substrate provides significant improvement in lithographic performance of the photoresist. Typically, the bottom antireflective coating is applied on the substrate and baked followed by application of a layer of photoresist. The photoresist is imagewise exposed and developed. The antireflective coating in the exposed area is then typically dry etched using various etching gases, and the photoresist pattern is thus transferred to the substrate.

Underlayers containing high amount of refractory elements can be used as hard masks as well as antireflective coating. Hard masks are useful when the overlying photoresist is not capable of providing sufficient resistance to dry etching that is used to transfer the image into the underlying semiconductor substrate. In such circumstances a material called a hard mask whose etch resistance is sufficient to transfer any patterns created over it into the underlying semiconductor substrate. This is made possible because the organic photoresist is different than the underlying hard mask and it is possible to find an etch gas mixture which will allow the transfer of the image in the photoresist into the underlying hard mask. This patterned hard mask can then be used with appropriate etch conditions and gas mixtures to transfer the image from the hard mask into the semiconductor substrate, a task which the photoresist by itself with a single etch process could not have accomplished.

Multiple antireflective layers and underlayers are being used in new lithographic techniques. In cases where the photoresist does not provide sufficient dry etch resistance, underlayers and/or antireflective coatings for the photoresist that act as a hard mask and are highly etch resistant during substrate etching are preferred. One approach has been to incorporate silicon, titanium or other metallic materials into a layer beneath the organic photoresist layer. Additionally, another high carbon content antireflective or mask layer may be placed beneath the metal containing antireflective layer, such as a trilayer of high carbon film/hardmask film/photoresist is used to improve the lithographic performance of the imaging process. Conventional hard masks can be applied by chemical vapor deposition, such as sputtering. However, the relative simplicity of spin coating versus the aforementioned conventional approaches makes the development of a new spin-on hard mask or antireflective coating with high concentration of metallic materials in the film very desirable.

The present invention relates to metal hardmasks for via or trench filling. In this process a photoresist pattern containing trenches and/or vias is coated with a metal hardmask filling in the trenches and/or vias. In this process overcoating of the photoresist features occurs during via/trench filling, this overcoat may be removed either by employing a short exposure with a plasma which erodes the hardmask faster (e.g. a fluorine based plasma etch for Si containing hardmask materials, or for other refractory metal based hardmasks which form volatile fluorides upon exposure to the fluorine plasma), by etching with a chemical solution, or by employing chemical mechanical polishing. These filled photoresist trenches and/or vias form a negative tone hardmask which acts as an etch barrier when the non-filled areas of photoresist are removed with an appropriate plasma such as an oxygen plasma which removes the photoresist faster than the hardmask filled areas to affect image tone reversal. Underlayer compositions for semiconductor applications containing metal oxides provide dry etch resistance as well as antireflective properties. Conventional soluble metal compounds to form metal oxide films, such as metal alkoxides, however, have been found to be very unstable to moisture in air creating a variety of issues, including shelf life stability, coating problems and performance shortcomings. Metal oxides have solubility problems in solvents typically used and accepted in the semiconductor industry. Thus there is an outstanding need to prepare spin-on hardmask, and other underlayers that contain organic solvent soluble, stable metal compounds even after exposure to air, which can act either as via or trench filling materials for patterned photoresist substrate acting as a negative tone hard mask to yield, after using an oxygen based plasma etching, a reverse tone image of the original photoresist pattern, or which can be coated on a substrate such as a carbon hardmask and then after curing, coated with a photoresist, patterning the photoresist using it as a mask to form using wet or plasma etching (e.g. fluorine based plasma) to form a positive tone metal oxide hardmask which can be transferred into the substrate using an appropriate plasma (eg oxygen). It is desirable that the metal oxide hardmask material be strippable by chemical solutions either after plasma transfer of the hardmask with an oxygen based plasma during negative tone transfer or positive tone transfer, or after curing prior to the application of the resist prior to the hardmask prior in positive tone transfer of the hardmask as described above.

SUMMARY OF THE DISCLOSURE

The present invention relates to novel, soluble, multi-ligand-substituted metal oxide compounds to form metal oxide films with improved stability as well as compositions made from them and methods of their use.

The invention relates to a soluble, multi-ligand-substituted metal compound having the following structure (I):

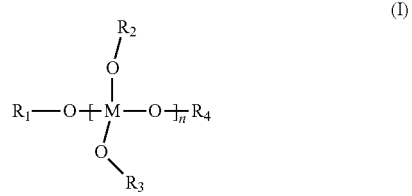

wherein M is a metal and n is 1 to 20, and wherein at least one of $R_1$, $R_2$, $R_3$, and $R_4$ is i) and at least at least one of $R_1$, $R_2$, $R_3$, and $R_4$ is ii), where i) is a silicon bearing organic moiety having at least 2 carbons, and ii) is an organic moiety (II),

wherein $R_8$ is selected from a group consisting of $C_2$-$C_{10}$ alkylene, $C_3$-$C_{12}$ branched alkylene, $C_5$-$C_{12}$ cycloalkylene, $C_2$-$C_{10}$ alkylene containing a C=C double bond, $C_3$-$C_{12}$ branched alkylene containing a C=C double bond, and a $C_5$-$C_{12}$ cycloalkylene containing a C=C double bond, and $R_9$ is hydrogen or the alkyloxycarbonyl moiety (III), where $R_{10}$ is a $C_1$-$C_8$ alkyl group,

provided that the silicon bearing moiety bearing an organic moiety having at least 2 carbons i) ranges from about 10 mole % to about 80 mole %, and the organic moiety ii) ranges from about 20 mole % to about 90 mole % of the total groups $R_1$, $R_2$, $R_3$, and $R_4$. Further, one of $R_1$, $R_2$, $R_3$, and $R_4$ can additionally be a $C_1$-$C_8$ alkyl groups where the content of this group can range from about 0 to 50 weight % (wt %).

The present invention also relates to composition which may be formulated with the multi-ligand-substituted metal compound having structure I into a spin-coatable composition by dissolving the solid components into a solvent or a solvent mixture containing alcohol, ester, ketone, lactone, diketones, aromatic moieties, carboxylic acid or an amide, such that the solid content in the composition is about 1-40%. The novel composition may also contain surfactants with a weight % ranging from about 0.01% to about 1 wt % in the total composition.

The present invention further relates to processes using novel compositions formulated with the novel multi-ligand-substituted metal compound with structure I to form a coating on a patterned substrate. Further the novel coating is patterned by heating the coated film at a temperature of 90-200° C. for 30-120 seconds such that the coated film baked film contains 10-60 weight % total oxide. The invention also relates to using this filled photoresist pattern as a negative tone hardmask where the non-filled areas of photoresist are removed with an appropriate plasma such as an oxygen plasma to cause image tone reversal. The invention also relates to removing the composition using a stripper, after baking and plasma transfer of the hardmask.

DETAILED DESCRIPTION

As used herein, the conjunction "and" is intended to be inclusive and the conjunction "or" is not intended to be exclusive unless otherwise indicated. For example, the phrase "or, alternatively" is intended to be exclusive.

As used herein, the term "and/or" refers to any combination of the foregoing elements including using a single element.

As used herein the term "alkyl" refers to straight, or cyclic chain alkyl substituents as well as any of their branched isomers.

As used herein the term "alkylene" refers to straight chain di-functionalized alkylene substituents having the general formula, —$(CH_2)_n$—, where n is an integer greater than 0.

As used herein the term "branched alkylene" refers to an alkylene substituent which has alkyl substituents present.

As used herein the term "cyclic alkylene" refers a disubstituted hydrocarbon moiety containing a cyclic hydrocarbon, the attachment points may either be on the cyclic hydrocarbon itself or on a pendant hydrocarbon substituent on the cyclic hydrocarbon.

As used herein the term "aryl" refers to refers to any functional group or substituent derived from an aromatic ring, such as phenyl, naphthyl, thienyl, indolyl etc.

As used herein the term "diketone" refers to any solvent having two ketone groups non limiting examples are diacetyl, acetylacetone, and hexane-2,5-dione.

As used herein the term "silicon-based polymer" refers to silicon polymers as well as organosilicon polymers and include the lower mer materials such as dimer, trimer and the like.

As used herein the terms "composition" and "formulation" are used interchangeable and mean the same thing.

Disclosed and claimed herein are soluble, multi-ligand-substituted metal compounds of the following structure (I):

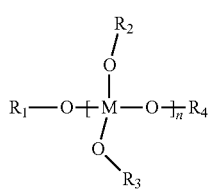

wherein M is a metal and n is 1 to 20, and wherein at least one of $R_1$, $R_2$, $R_3$, and $R_4$ is i) and at least at least one of $R_1$, $R_2$, $R_3$, and $R_4$ is ii), where i) is a silicon bearing organic moiety having at least 2 carbons, and ii) is an organic moiety (II),

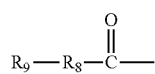

wherein $R_8$ is selected from a group consisting of $C_2$-$C_{10}$ alkylene, $C_3$-$C_{12}$ branched alkylene, $C_5$-$C_{12}$ cycloalkylene, $C_2$-$C_{10}$ alkylene containing a C=C double bond, $C_3$-$C_{12}$ branched alkylene containing a C=C double bond, and a $C_5$-$C_{12}$ cycloalkylene containing a C=C double bond, and $R_9$ is hydrogen or the alkyloxycarbonyl moiety (III), where $R_{10}$ is a $C_1$-$C_8$ alkyl group,

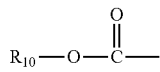

provided that the silicon bearing moiety bearing an organic moiety having at least 2 carbons i) ranges from about 10 mole % to about 80 mole %, and ii) ranges from about 20 mole % to about 90 mole % of the total groups $R_1$, $R_2$, $R_3$, and $R_4$. The metal, M, can be chosen from a list of suitable metals, including, for example, titanium, zirconium, tantalum, lead, antimony, thallium, indium, ytterbium, gallium, hafnium, aluminum, magnesium, molybdenum, germanium, tin, iron, cobalt, nickel, copper, zinc, gold, silver, cadmium, tungsten, or platinum as well as other transition metals. The metal compound may be monoatomic, n being about 1. The metal compound may also be polyatomic, n being about 2 to about 20, creating a chain of alternating metal-oxygen segments. The polyatomic compound may contain only one type of metal atom, such as, for example, titanium, or they may have other metals incorporated into the metal-oxo backbone, such as silicon and zirconium. The amount of each metal in a mixed metal polyatomic metal compound can range from 0.001% to 99.999% depending on the desired characteristics of the final remaining metal oxide layer. These novel metal compounds are stable even after exposure to air, for up to 24 hours and then stored for at least 1 week, have good filling properties and are also strippable in chemical solutions.

In one embodiment the metals for the multi-ligand-substituted metal compound of structure (I) are selected from a group consisting of titanium, zirconium and hafnium. One example of the metal is titanium.

In one embodiment, the novel compounds are the ones in which the soluble, multi-ligand-substituted metal compounds of structure (I), have the silicon bearing moiety bearing an organic moiety having at least 2 carbons i) present in a content between about 30 mole % to about 60 mole %, and also have the organic moiety ii) present in a content between about 30 mole % to about 60 mole % based on the total number of groups $R_1$, $R_2$, $R_3$, and $R_4$.

In another embodiment the soluble, multi-ligand-substituted metal compound has the following structure (I):

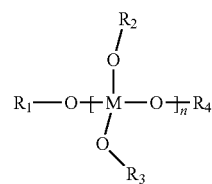

wherein M is a metal and n is 1 to 20, and wherein at least one of $R_1$, $R_2$, $R_3$, and $R_4$ is i), at least one of $R_1$, $R_2$, $R_3$, and $R_4$ is ii), and at least one of $R_1$, $R_2$, $R_3$, and $R_4$ is a $C_1$-$C_8$ alkyl moiety, further where i) is a silicon bearing organic moiety having at least 2 carbons, and ii) is an organic moiety (II),

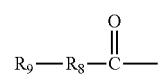

wherein $R_8$ is selected from a group consisting of $C_2$-$C_{10}$ alkylene, $C_3$-$C_{12}$ branched alkylene, $C_5$-$C_{12}$ cycloalkylene, $C_2$-$C_{10}$ alkylene containing a C=C double bond, $C_3$-$C_{12}$ branched alkylene containing a C=C double bond, and a $C_5$-$C_{12}$ cycloalkylene containing a C=C double bond, and $R_9$ is hydrogen or the alkyloxycarbonyl moiety (III), where $R_{10}$ is a $C_1$-$C_8$ alkyl group,

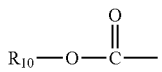

provided that the silicon bearing moiety bearing an organic moiety having at least 2 carbons i) ranges from about 10 mole % to about 80 mole %, and ii) ranges from about 20 mole % to about 90 mole % of the total groups $R_1$, $R_2$, $R_3$, and $R_4$. The $C_1$-$C_8$ alkyl moiety which is present ranges from above about 0 mole % to about 50 mole % of the total of the groups $R_1$, $R_2$, $R_3$, and $R_4$, or about 0 mole % to 35 mole % of the total of the groups $R_1$, $R_2$, $R_3$, and $R_4$.

The soluble, multi-ligand-substituted metal compounds of structure (I) described above may have more than one type of metal when n is 2 to 20.

In the soluble, multi-ligand-substituted metal compounds of structure (I) described above the silicon bearing organic moiety having at least 2 carbon i) is exemplified by the group consisting of a trisubstitutedsilyl moiety (IV) and a siloxane moiety (V)

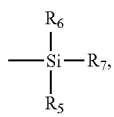

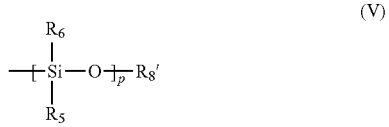

wherein $R_5$, and $R_6$, are independently selected from $C_1$-$C_8$ alkyl moieties, $C_3$-$C_{12}$ branched alkyl, aryl moiety, $R_7$ is independently selected from a $C_1$-$C_8$ alkyl moieties, aryl moieties and hydroxyl, and $R_{8'}$ is selected from a group consisting of hydrogen, a $C_1$-$C_8$ alkyl, a $C_1$-$C_8$ alkyl substituted with a hydroxyl group, a carboxylic acid group (—$CO_2H$) or an aryl moiety, and further where p represents the number of repeat units in the siloxane moiety (v) and p ranges from about 1 to 20.

In one embodiment the soluble, multi-ligand-substituted metal compound of structure (I) is where M is titanium, and n is 4 to 16, the organic moiety i) is chosen from the group consisting of

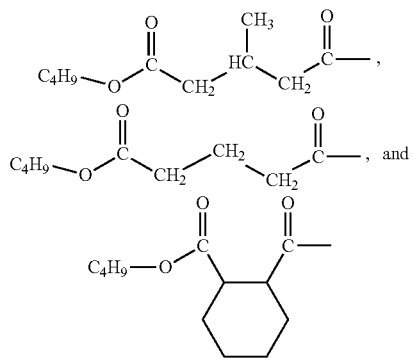

In another embodiment the soluble, multi-ligand-substituted metal compound of structure (I) is where M is titanium, and n is 4 to 16, the silicon bearing organic moiety ii) is chosen from the group consisting of

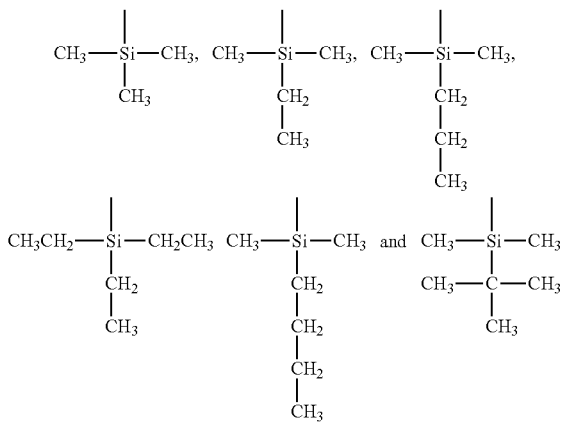

The novel multi-ligand-substituted metal compounds are prepared from their alkoxides or acetylacetonates (acac), as described below. The alkoy or acac metal compound is reacted with a SiOH containing compound (e.g. trimethylsilanol), oligomer or polymer (e.g. polydimethylsiloxane (with hydroxyl end groups)) which yield the silicon bearing organic moiety i) having at least 2 carbons, then followed by reaction with anhydride, cyclic anhydride or a carboxylic acid which yields the organic moiety (II). The optional $C_1$-$C_8$ alkyl substituent which may constitute some of the $R_1$, $R_2$, $R_3$, $R_4$ groups on the multi-ligand-substituted metal compound, may result either from using a residual alkoxide, or an alkoxide metal precursor or by using a $C_1$-$C_8$ alcohol as an additional reagent in the preparation of the multi-ligand-substituted metal compound. The reaction is done in a solvent which can dissolve both the alkoxide or acac precursor, and other reagents. Typical solvents or solvent mixtures for the reaction contain ester, ether or alcoholic functional groups, for instance a 70/30 by volume mixture of propylene glycol methyl ether acetate (PGMEA) and propolylene glycol methyl ether (PGME). Examples of other solvents which can be used are hydrocarbons such as cyclohexane, benzene, toluene, etc. It should be noted that more than two ligands may be used to react with the alkoxy metal as desired.

Disclosed herein also are novel compositions comprising novel compounds described herein which are dissolved in an organic solvent. The solvent may be chosen from a solvent or solvent mixture containing an alcohol, an ester, a ketone, a carboxylic acid, an amide, an aromatic moeity, or a diketone. Specific examples of suitable solvents are as follows:

Specific examples of suitable solvents are lower alcohols ($C_1$-$C_6$) such as isopropanol, n-butanol, t-butanol, 1-pentanol and 4-methyl-2-pentanol, a glycol such as ethylene glycol and propylene glycol, diketones such as diacetyl, acetylacetone, and hexane-2,5-dione, a glycol ether derivative such as ethyl cellosolve, methyl cellosolve, propylene glycol monomethyl ether, diethylene glycol monomethyl ether, diethylene glycol monoethyl ether, dipropylene glycol dimethyl ether, propylene glycol n-propyl ether, or diethylene glycol dimethyl ether; a glycol ether ester derivative such as ethyl cellosolve acetate, methyl cellosolve acetate, or propylene glycol monomethyl ether acetate; carboxylates such as ethyl acetate, n-butyl acetate and amyl acetate; carboxylates of di-basic acids such as diethyloxylate and diethylmalonate; dicarboxylates of glycols such as ethylene glycol diacetate and propylene glycol diacetate; and hydroxy carboxylates such as methyl lactate, ethyl lactate, ethyl glycolate, and ethyl-3-hydroxy propionate; a ketone ester such as methyl pyruvate or ethyl pyruvate; an alkoxy alcohol such as 1-Methoxy-2-propanol, 2-methoxyethanol, ethoxyethanol, an alkoxycarboxylic acid ester such as methyl 3-methoxypropionate, ethyl 3-ethoxypropionate, ethyl 2-hydroxy-2-methylpropionate, or methylethoxypropionate; a ketone derivative such as methyl ethyl ketone, acetyl acetone, cyclopentanone, cyclohexanone or 2-heptanone; a ketone ether derivative such as diacetone alcohol methyl ether; a ketone alcohol derivative such as acetol or diacetone alcohol; lactones such as butyrolactone and gamma-velaro lactone; an amide derivative such as dimethylacetamide or dimethylformamide, aromatic solvents such as anisole, and mixtures thereof.

The total solid content of the composition can range from about 1 to about 40 weight % or about 5 to about 30 weight %.

The multi-ligand-substituted metal compounds of the current disclosures are used to prepare metal oxide containing layers useful in the semiconductor industry as well as associated industries may be used in solvent without any further components.

However, the novel compositions comprising the novel compounds described herein, may include other components which enhance the performance of the coating, e.g. lower alcohols ($C_1$-$C_6$ alcohols), alkoxyalcohols, lactones, $C_1$-$C_{20}$ alkyl carboxylic acids, surface leveling agents or surfactants (<5 wt % of total solids or 0.01 to 1 wt % of total composition), dialkoxy bis(betadiketoesters) (1-20 wt % or 5-10 wt % of total solids), dialkoxy bis(beta diketone) (1-20 wt % or 5-10 wt % of total solids), thermal acid generator, photoacid generator, thermal base generators or thermal radical generators. Examples of dialkoxy bis(betadiketoesters) and dialkoxy bis(beta diketone) are acetylacetone, benzoylacetone, 4,4,4-Trifluoro-1-phenyl-1,3-butanedione, and ethyl acetoacetate; or optional polymer components such as, for example, poly(meth)acrylics, poly(meth)acrylates, and condensation polymers such as polyesters, novolac resins, siloxane resins or organosilsesquioxanes. These polymers may be used alone or in combination with each other depending on the desired properties of the final film after baking. These polymers are generally crosslinking polymers, containing any of a number of the same or different crosslinking substituents, such as, for example, epoxy, hydroxy, thiols, amines, amides, imides, esters, ethers, ureas, carboxylic acids, anhydrides, and the like. Other examples of crosslinking groups include the glycidyl ether group, glycidyl ester group, glycidyl amino group, methoxymethyl group, ethoxy methyl group, benzyloxymethyl group, dimethylamino methyl group, diethylamino methyl group, dimethylol amino methyl group, diethylol amino methyl group, morpholino methyl group, acetoxymethyl group, benzyloxy methyl group, formyl group, acetyl group, vinyl group and isopropenyl group.

Surface leveling agents or surfactants can be polyethylene glycol dodecyl ether, polyoxyethylene oleyl ether, polyethylene glycol octadecyl ether, polyethylene glycol tert-octylphenyl ether, fluorine based surfactant, and silicon based surfactant. Surfactants with the following trade names may be used, Brij30, Brij52, Triton X-100, FC4430, KP341, Tween 80 etc.

To further crosslink the composition, crosslinking additives may be added, including, for example, bisphenol A-based epoxy compounds, bisphenol F-based epox compounds, bisphenol S-based epoxy compounds, the novolac resin-based epoxy, poly(hydroxystyrene)-based epoxy compounds, melamine compounds, benzoguanamine compounds, and urea compounds.

Thermally activated catalysts, such as thermal acid generators, may also be added to the composition to aid in crosslinking during thermal curing of the coated composition. The thermal acid generator can be activated at above 90° C. for example above 120° C., and above 150° C. Examples of thermal acid generators include metal-free sulfonium salts and iodonium salts, such as triarylsulfonium, dialkylarylsulfonium, and diarylakylsulfonium salts of strong non-nucleophilic acids alkylaryliodonium, diaryliodonium salts of strong non-nucleophilic acids; and ammonium, alkylammonium, dialkylammonium, trialkylammonium, tetraalkylammonium salts of strong non nucleophilic acids. 2-nitrobenzyl esters of alkyl or arylsulfonic acids and other esters of sulfonic acid which thermally decompose to give free sulfonic acids. Other examples include diaryliodonium perfluoroalkylsulfonates, diaryliodonium tris(fluoroalkylsulfonyl)methide, diaryliodonium bis(fluoroalkylsulfonyl)methide, diaryliodonium bis(fluoroalkylsulfonyl)imide, diaryliodonium or quaternary ammonium perfluoroalkylsulfonate. Examples of labile esters: 2-nitrobenzyl tosylate, 2,4-dinitrobenzyl tosylate, 2,6-dinitrobenzyl tosylate, 4-nitrobenzyl tosylate; benzenesulfonates such as 2-trifluoromethyl-6-nitrobenzyl 4-chlorobenzenesulfonate, 2-trifluoromethyl-6-nitrobenzyl 4-nitro benzenesulfonate; phenolic sulfonate esters such as phenyl, 4-methoxybenzenesulfonate; quaternary ammonium tris(fluoroalkylsulfonyl)methide, and quaternaryalkyl ammonium bis(fluoroalkylsulfonyl)imide, alkyl ammonium salts of organic acids, such as triethylammonium salt of 10-camphorsulfonic acid. A variety of aromatic (anthracene, naphthalene or benzene derivatives) sulfonic acid amine salts can be employed as the TAG, including those disclosed in U.S. Pat. Nos. 3,474,054, 4,200,729, 4,251,665 and 5,187,019. The TAG may have a very low volatility at temperatures between 170-220° C.

Thermally activated peroxides may also be used in the current composition, such as, for example, benzoyl peroxide, 3,5-dichlorobenzoperoxide and the like.

The compositions of the current disclosure contain greater than 20 weight % of the multi-ligand-substituted metal compound based on solids, such as, for example, greater than 50 weight % or greater than 90 weight % based on solids. Two or more metal compounds with the same or different metal can be used in formulations. The optional polymer component, (see detailed description of polymer above) when used, is less than about 80 weight % based on solids, such as, for example, less than 50 weight %, less than 10 weight % based on solids. The crosslinking additive is present between 2 to 30 weight % based on solids. Other additives typical of coating additive may be added, such as, for example, wetting agents, surfactants, anti-foam agent, thixotropic agents and the like.

The total percent solids in the chosen solvent or solvent blend is between about 1 to 40 weight %, such as, for example, about 5 to 30% weight %.

The novel compound and compositions made comprising the novel compound are stable when exposed to air and then stored. The materials may be exposed to air for up to 24 hours and then stored for at least 1 week without any deterioration of lithographic properties, such as coating defects. Furthermore, the novel materials can be removed by wet strippers, such as chemical solutions that remove the baked film.

The compositions of the current disclosure can be coated onto the surface of a substrate such as low dielectric constant materials, silicon, silicon substrates coated with a metal surface, copper coated silicon wafer, copper, aluminum, polymeric resins, silicon dioxide, metals, doped silicon dioxide, silicon nitride, tantalum, polysilicon, ceramics, aluminum/copper mixtures, any of the metal nitrides such as AlN; gallium arsenide and other such Group III/V compounds. The substrate may also be other antireflective coatings or underlayers, such as high carbon underlayers coated over the above mentioned substrates. The substrate may comprise any number of layers made from the materials described above.

The composition may also be coated onto a patterned substrate using techniques well known to those skilled in the art as described above. The patterned substrate may be any patterned substrate for instance as a non limiting example a photoresist patterned with features comprised of vias, trenches, holes, and/or other hollow topographical features. The film thickness of the coating on patterned substrates ranges from about 20 nm to about 600 nm, such as, for example, about 60 nm to about 400 nm depending on the depth of topographical features in the resist. The coating may be further heated on a hot plate or convection oven for a sufficient length of time to remove a majority of the solvent and optionally to induce curing. The baking temperature may be from about 90° C. to about 250° C. for about 30 seconds to about 5 minutes, such as, for example, from about 110° C. to about 200° C. for about 1 to about 2 minutes. The composition of the film contains between about 10 to about 50 wt % of total oxide or between about 20 to about 35 wt % of total oxide at normal baking conditions.

The baked metal oxide film or residual hard mask, after oxygen plasma based pattern transfer, can be advantageously removed using a chemical stripping agent, such as acid, base, peroxide, and mixture thereof. For example, 85% phosphoric acid, diluted sulfuric acid, 3% HF, 10% TMAH, 10% hydrogen peroxide, aqueous alkaline peroxides and mixtures thereof. Stripping time ranges from about 5 seconds to about 120 seconds at about room temperature to about 70° C. depending on the film curing conditions. Other stripping processes may be employed in conjunction with processing conditions of the metal oxide film. For example, when the film is baked at a lower temperature or a shorter time, the stripper may be diluted, the time may be shortened and/or the temperature of stripping may be reduced or alternatively when baked at low temperature without a crosslinking agent (i.e. not cured) the baked coating may be strippable with the original coating solvent.

The soluble, multi-ligand-substituted metal compounds of the current disclosure, their compositions and methods of use can also be used to prepare antireflective coatings. In this application sufficient chromophore groups (e.g. aryl groups or alkyl, branched alkyl or cycloalkyl group containing a carbon carbon double bond) must be present, such that the refractive indices n (refractive index) ranges from about 1.4 to about 2.0 while k (extinction coefficient) (part of the complex refractive index $n_c=n-jk$) ranges from about 0.1 to about 0.8 at 193 nm exposure wavelength. The n and k values can be calculated using an ellipsometer, such as the J. A. Woollam WVASE VU-32™ Ellipsometer. The exact values of the optimum ranges for k and n are dependent on the exposure wavelength used and the type of application. Typically for 193 nm the preferred range for k is about 0.1 to about 0.8, and for 248 nm the preferred range for k is about 0.15 to about 0.8, however, other exposure wavelengths such as, for example DUV and beyond DUV can be used and the compositions tuned to work in conjunction with them.

In one application of this invention the photoresist was initially coated on the novel coating itself while in the other application the novel coating was applied to an imaged resist film containing vias and/or trenches to act as a filling compound.

Photoresists can be any of the types used in the semiconductor industry, provided the photoactive compound in the photoresist and the antireflective coating substantially absorb at the exposure wavelength used for the imaging process. Photoresists useful for immersion lithography are preferred. Typically, photoresists suitable for imaging with immersion lithography may be used, where such photoresists have a refractive index higher than 1.85 and also are hydrophobic having water contact angle in the range of 75° to 95°.

To date, there are several major deep ultraviolet (uv) exposure technologies that have provided significant advancement in miniaturization, and have actinic radiation of 250 nm to 10 nm, such as 248 nm, 193 nm, 157 and 13.5 nm. Chemically amplified photoresist are often used. Photoresists for 248 nm have typically been based on substituted polyhydroxystyrene and its copolymers/onium salts, such as those described in U.S. Pat. No. 4,491,628 and U.S. Pat. No. 5,350,660. On the other hand, photoresists for exposure at 193 nm and 157 nm require non-aromatic polymers since aromatics are opaque at this wavelength. U.S. Pat. No. 5,843,624 and U.S. Pat. No. 6,866,984 disclose photoresists useful for 193 nm exposure. Generally, polymers containing alicyclic hydrocarbons are used for photoresists for exposure below 200 nm. Alicyclic hydrocarbons are incorporated into the polymer for many reasons, primarily since they have relatively high carbon to hydrogen ratios which improve etch resistance, they also provide transparency at low wavelengths and they have relatively high glass transition temperatures. U.S. Pat. No. 5,843,624 discloses polymers for photoresist that are obtained by free radical polymerization of maleic anhydride and unsaturated cyclic monomers. Any of the known types of 193 nm photoresists may be used, such as those described in U.S. Pat. No. 6,447,980 and U.S. Pat. No. 6,723,488, and incorporated herein by reference. Two basic classes of photoresists sensitive at 157 nm, and based on fluorinated polymers with pendant fluoroalcohol groups, are known to be substantially transparent at that wavelength. One class of 157 nm fluoroalcohol photoresists is derived from polymers containing groups such as fluorinated-norbornenes, and are homopolymerized or copolymerized with other transparent monomers such as tetrafluoroethylene (U.S. Pat. No. 6,790,587, and U.S. Pat. No. 6,849,377) using either metal catalyzed or radical polymerization. Generally, these materials give higher absorbencies but have good plasma etch resistance due to their high alicyclic content. More recently, a class of 157 nm fluoroalcohol polymers was described in which the polymer backbone is derived from the cyclopolymerization of an asymmetrical diene such as 1,1,2,3,3-pentafluoro-4-trifluoromethyl-4-hydroxy-1,6-heptadiene (U.S. Pat. No. 6,818,258) or copolymerization of a fluorodiene with an olefin (U.S. Pat. No. 6,916,590). These materials give acceptable absorbance at 157 nm, but due to their lower alicyclic content as compared to the fluoro-norbornene polymer, have lower plasma etch resistance. These two classes of polymers can often be blended to provide a balance between the high etch resistance of the first polymer type and the high transparency at 157 nm of the second polymer type. Photoresists that absorb extreme ultraviolet radiation (EUV) of 13.5 nm are also useful and are known in the art. Thus photoresists absorbing in the range of about 12 nm to about 250 nm are useful. The novel coatings can also be used in process with nanoimprinting and e-beam resists.

After the coating process, the photoresist is imagewise exposed. The exposure may be done using typical exposure equipment. The exposed photoresist is then developed in an aqueous developer to remove the treated photoresist. The developer is preferably an aqueous alkaline solution comprising, for example, tetramethylammonium hydroxide (TMAH), typically 2.38 weight % TMAH. The developer may further comprise surfactant(s). An optional heating step can be incorporated into the process prior to development and after exposure.

The process of coating and imaging photoresists is well known to those skilled in the art and is optimized for the specific type of photoresist used. The photoresist patterned substrate can then be dry etched with an etching gas or mixture of gases, in a suitable etch chamber to remove the exposed portions of the underlayers and optional other antireflective coatings. Various etching gases are known in the art for etching underlayer coatings, such as those comprising $O_2$, $CF_4$, $CHF_3$, $Cl_2$, HBr, $SO_2$, CO, etc.

In one embodiment, the article comprises a photoresist substrate patterned with vias and/or trenches, over which the novel the metal oxide composition of the current disclosure is coated. The photoresist was initially imaged to produce vias and/or trenches as disclosed above. The photoresist film with vias, trenches, holes or other hollow topographical features patterned in the in to it has these features filled with the novel composition of the current disclosure. This is done by coating the metal oxide composition of the current disclosure onto the patterned resist and baking the film. Then, any composition of the current disclosure overlaying the top of the patterned resist is removed by either, etching it away employing a fluorine based plasma, by etching with a chemical solution, or by chemical mechanical polishing. The vias trenches, holes and/or other hollows topographical features filled with the composition of the current disclosure where the top of the resist features are free of the composition of the current disclosure are then dry plasma etched using gases comprising oxygen using the metal oxide filled vias, trenches, holes or other filled hollow topgraphical resist features as a hard mask to form a negative tone image in the substrate of the original patterned photoresist by selectively removing the resist areas not filled with the composition of the current disclosure.

Advantageously, after plasma transfer of the image to the substrate, the residual composition of the current disclosure can be removed using a chemical stripping agent, such as the original casting solvent, acid, base, peroxide, and mixture thereof. For example, 85% phosphoric acid, diluted sulfuric acid, 3% HF, 10% TMAH, 10% hydrogen peroxide, aqueous alkaline peroxides and mixtures thereof. Stripping time ranges from about 5 seconds to about 120 seconds at about room temperature to about 70° C. depending on the film curing conditions. Other stripping processes may be employed in conjunction with processing conditions of the metal oxide film. For example, when the film is b at a lower temperature or a shorter time, the stripper may be diluted, the time may be shortened and/or the temperature of stripping may be reduced. If the film is not cured (i.e crosslinked), the metal hard mask can be removed with the casting solution.

Each of the documents referred to above are incorporated herein by reference in its entirety, for all purposes. The following specific examples will provide detailed illustrations of the methods of producing and utilizing compositions of the present invention. These examples are not intended, however, to limit or restrict the scope of the invention in any way and should not be construed as providing conditions, parameters or values which must be utilized exclusively in order to practice the present invention.

EXAMPLES

The refractive index (n) and the extinction coefficient (k) values of the examples metal oxide coatings below were measured on a J. A. Woollam VASE32 ellipsometer.

Thermogravetric measurements use to measure Ti wt % were done using A Perkin Elmer Thermogravimetric Analyzer TGA7 with heating from 50° C. to 800° C. at a heating rate of 120° C./min in a $O_2$ atmosphere and maintaining this temperature for 60 minutes.

Elemental analysis used to measure Ti wt % and Si content were done by Intertek of Whitehouse N.J.

Synthesis Example 1

40 g of Titanium(IV) butoxide polymer (Ti(IV)BTP polymer) (Sigma-Aldrich Corporation, St Louis Mo.), was dissolved in 52 g of 70/30 PGMEA/PGME solvent and poured into the reaction vessel under $N_2$. This solution was stirred and its temperature raised to 50° C. while trimethylsilanol 12 g was added dropwise under $N_2$. The reaction mixture was kept at 60 C for 2 hours, after which time 20 g of 1,2-cyclohexanedicarboxylic anhydride and 20 g of 70/30 PGMEA/PGME were mixed with the above reaction mixture and the reaction was continued at 60° C. for about one hour. After cooling down to room temperature overnight, the product was stored in a brown bottle and sealed carefully. FT-IR spectrum of the product solution was taken in cyclohexane. The resonance at 970 cm-1 was assigned to Ti—O—Si stretching frequency. The measured total metal oxide content was 28 wt % in films after baking at 150° C. for 60 s.

Synthesis Example 2

40 g of Ti(IV)BTP polymer was dissolved in 58 g of 70/30 PGMEA/PGME solvent and poured into the reaction vessel under $N_2$. The temperature was raised to 50° C. while stirring and trimethylsilanol 18 g was added dropwise under $N_2$. The reaction was kept at 60° C. for 2 hours. Then 20 g of 1,2-cyclohexanedicarboxylic anhydride and 20 g of 70/30 PGMEA/PGME solvent was mixed with the reaction mixture and the reaction was continued at 60° C. for about one hour. After cooling down to room temperature overnight, the product was stored in a brown bottle and sealed carefully. The measured total metal oxide content was 32 wt % in films after baking at 150° C. for 60 s.

Synthesis Example 3

20 g of Ti(IV)BTP polymer was dissolved in 25 g of 70/30 PGMEA/PGME solvent and poured into the reaction vessel under $N_2$. The temperature was raised to 50° C. stirring while tertbutyldimethylsilanol 4.5 g was added dropwise while stirring under $N_2$. The reaction was kept at 60 C for 2 hours. Then 5 g of 1,2-cyclohexanedicarboxylic anhydride and 5 g of 70/30 PGMEA/PGME solvent were mixed into the reaction mixture and the reaction was continued at 60 C for about one hour. After cooling down to room temperature overnight, the product was stored in a brown bottle and sealed carefully.

Synthesis Example 4

40 g of Ti(IV)BTP polymer was dissolved in 52 g of 70/30 PGMEA/PGME solvent and poured into the reaction vessel under $N_2$. The temperature was raised to 50° C. stirring while trimethylsilanol 12 g was added dropwise in above TiBTP solution with stirring under $N_2$. The reaction was kept at 60 C for 2 hours, after which time 15.2 g of glutaric anhydride and 15.2 g of ArF thinner solvent were then mixed with the above reaction mixture and the reaction was continued at 60 C for about one hour. After cooling down to room temperature overnight, the product was stored in a brown bottle and sealed carefully.

Synthesis Example 5

40 g of Ti(IV)BTP polymer was dissolved in 44 g of 70/30 PGMEA/PGME solvent and poured into the reaction vessel under $N_2$. The temperature was raised to 50° C. stirring while 4 g of polydimethylsiloxane (hydroxy ended) was added with stirring under $N_2$. The reaction was kept at 60° C. for 2 h. Then 20 g of 1,2-cyclohexanedicarboxylic anhydride and 20 g of ArF thinner solvent were mixed with the above reaction mixture and the reaction was continued at 60° C. for about one hour. After cooling down to room temperature overnight, the product was stored in a brown bottle and sealed carefully.

Synthesis Example 6

40 g of Ti(IV)BTP polymer was dissolved in 58 g of ArF thinner solvent and poured into the reaction vessel under $N_2$. The temperature was raised to 50° C. stirring while trimethylsilanol 18 g was added dropwise in above TiBTP solution with stirring under $N_2$. The reaction was kept at 60° C. for 2 hours, after which time, 30 g of 1,2-cyclohexanedicarboxylic anhydride and 30 g of ArF thinner solvent were then mixed with the above reaction mixture and the reaction was continued at 60° C. for about one hour. After cooling down to room temperature overnight, the product was stored in a brown bottle and sealed carefully. The measured total metal oxide content was 25 wt % in films at 150° C./60 s baking conditions.

Synthesis Example 7

40 g of Ti(IV)BTP polymer was dissolved in 61 g of ArF thinner solvent and poured into the reaction vessel under $N_2$. The temperature was raised to 50° C. stirring while trimethylsilanol 21 g was added dropwise in above TiBTP solution with stirring under $N_2$. The reaction was kept at 60° C. for 2 hours, after which time, 35 g of 1,2-cyclohexanedicarboxylic anhydride and 35 g of ArF thinner solvent were then mixed with the above reaction mixture and the reaction was continued at 60° C. for about one hour. After cooling down to room temperature overnight, the product was stored in a brown bottle and sealed carefully. The measured total metal oxide content was 23 wt % in films at 150° C./60 s baking conditions.

Comparison Synthesis Example 1

40 g of Ti(IV)BTP polymer, 30 g of citraconic anhydride and 70 g of PGMEA/PGME 70:30 were mixed by stirring and heated in a flask under nitrogen. The reaction was maintained at 50° C. for about 4 hours. After cooling down to room temperature, the product with 50% solid content was stored in a brown bottle. The measured total metal oxide content was 28 wt % in films at 150° C./60 s baking conditions.

Formulation and Coating Example 1

A 10 wt % solution of metal polymer from Synthesis Example 1 was prepared in PGMEA/PGME 70:30 solvent. After sufficient mixing, the solution was spin-coated on the silicon wafer and baked at 150° C. for 60 seconds. The refractive index (n) and the absorption (k) values of the antireflective coating were measured to be n=1.67 and k=0.19 on a J. A. Woollam VASE32 ellipsometer.

Formulation and Coating Example 2

A 10 wt % solution of metal polymer from Synthesis Example 2 was prepared in PGMEA/PGME 70:30 solvent. After sufficient mixing, the solution was spin-coated on the silicon wafer and baked at 150° C. for 60 seconds. The refractive index (n) and the absorption (k) values of the antireflective coating were measured to be n=1.67 and k=0.18 on a J. A. Woollam VASE32 ellipsometer.

Formulation and Coating Example 3

A 10 wt % solution of metal polymer from Synthesis Example 6 was prepared in PGMEA/PGME 70:30 solvent. 0.2 wt % of FC4430 surfactant in total composition was added to the solution. After sufficient mixing, the solution was spin-coated on the silicon wafer and baked at 150 C for 60 seconds. The refractive index (n) and the absorption (k) values of the antireflective coating were measured to be n=1.66 and k=0.13 on a J. A. Woollam VASE32 ellipsometer.

Formulation and Coating Example 4

A 10 wt % solution of metal polymer from Synthesis Example 7 was prepared in PGMEA/PGME 70:30 solvent. 0.2 wt % of FC4430 surfactant in total composition was added to the solution. After sufficient mixing, the solution was spin-coated on the silicon wafer and baked at 150° C. for 60 seconds. The refractive index (n) and the absorption (k) values of the antireflective coating were measured to be n=1.68 and k=0.14 on a J. A. Woollam VASE32 ellipsometer.

Comparison Formulation Example 1

A 10 wt % solution of metal polymer from Comparison Synthesis Example 1 was prepared in PGMEA/PGME 70:30 solvent. After sufficient mixing, the solution was spin-coated on the silicon wafer and bake at 150° C. for 60 seconds. The refractive index (n) and the absorption (k) values of the antireflective coating were measured to be n=1.59 and k=0.48 on a J. A. Woollam VASE32 ellipsometer.

Determination of Ti wt % in Baked Films

The Ti wt % in the metallic underlayer films were measured by elemental analysis and TGA (Thermogravetric Analysis) weight loss measurement. The results from two methods were consistent. The measured total oxide content ranged from 20 to 40 wt % in films baked at 150° C./60 s or 160° C./60 s. The film mostly comprised of titanium compounds with insignificant silicon content based on elemental analysis.

Trench Filling Performance Evaluation Example 1

The solution of Formulation Example 1 with the adjusted solid content targeting final film thickness of 110 nm was spin-coated on a patterned wafer with trench size of 70 nm (depth)×30 nm (width) and line/space (L/S) 1:1 at a spin speed of 1500 rpm. The coated wafer was subsequently baked at 150° C./60 s. The Cross-section scanning electron microscope (XSEM) data showed excellent film coating quality and good filling performances. The final film thickness was 115 nm over the bottom of the trench area.

Via Filling Performance Evaluation Example 1

The solution of Formulation Example 7 with the adjusted solid content targeted for a final film thickness of 250 nm was spin-coated on a deep via substrate at a spin speed of 1500 rpm. The via wafer used had 650 nm deep vias with ~90 nm via size. The coated wafer was subsequently baked at 150° C./60 s. The XSEM data showed excellent film coating quality and good filling performances for both isolated and dense areas.

Comparison Trench Filling Performance Evaluation Example 1

The solution of Comparison Formulation Example 1 with the adjusted solid content targeted for a final film thickness of 110 nm was spin-coated on a patterned wafer with trench size of 70 nm (depth)×30 nm (width) and L/S 1:1 at a spin speed of 1500 rpm. The coated wafer was subsequently baked at 150° C./60 s. The XSEM data show voids in filling performances.

Etch Rate for Coatings Prepared Based on Formulation and Coating

Coating Example 1 & 2 in $CF_4$ and $O_2$ Etch Gasses 20.0 wt % formulation solution for Coating Example 1 and 20.0 wt % formulation solution for Coating Example 2 were prepared for etch rate tests. The coated wafer was then heated on a hot plate for 1 minute at 150° C. AZ®2110P photoresist (available from AZ® Electronic Materials USA Corp, 70 Meister Ave, Somerville, N.J.) was baked for 1 minute at 100° C. and used as a reference. All experiments were carried out without patterned photoresist on top using NE-5000N (UL- VAC) instrument. The etch rates of various materials were measured using conditions summarized in Table 1.

TABLE 1

| RF POWER | 500 W(ISM)/250 W(Bias) | RF POWER | 200 W(ISM)/100 W(Bias) |
|---|---|---|---|
| Gas Flow | $CF_4$ = 20 sccm | Gas Flow | $O_2/N_2$/Ar = 10/10/15 sccm |
| Pressure | 10 Pa | Pressure | 0.67 Pa |
| Etching Time | 10 sec | Etching Time | 10 sec |
| Back He Temp | 20° C. | Back He Temp | 20° C. |

TABLE 2

| | Etch rate (nm/min) | | Etch rate ratio to Resist | | Etch selectivity |
|---|---|---|---|---|---|
| Materials | $CF_4$ | $O_2/N_2$/Ar | $CF_4$ | $O_2/N_2$/Ar | $CF_4/(O_2/N_2/Ar)$ |
| AZ ®2110P resist | 130.5 | 350.1 | 1.0 | 1.0 | 0.37 |
| Coating Example 1 | 393.9 | 140.3 | 3.0 | 0.4 | 2.8 |
| Coating Example 2 | 361.2 | 135.9 | 2.8 | 0.39 | 2.7 |

As shown in Table 2, the etch rates of coating examples 1 and 2 were significantly lower than that of photoresist (~40%) in oxygen gas. Also, the Etch Rate Ratios of either Coating Example 1 or 2 to the resist AZ®2110P towards oxygen, demonstrates the resistance of the novel materials of this invention towards an oxygen based plasma. Furthermore, the Etch selectively listed in Table 2 demonstrates that the novel material have high etch resistance in oxygen while maintaining a high etch rate in a fluorine based plasma. This indicates that the metal containing composition of this invention can be used as a hardmask in pattern transfer from resist to substrate. This good etch behavior in materials which also have good filling properties and good stability are an unexpected coupling of desirable properties.

We claim:

1. A soluble, multi-ligand-substituted metal compound of structure (I):

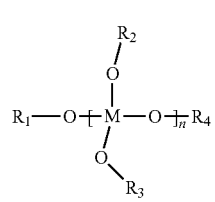

(I)

wherein M is a metal and n is 1 to 20, and wherein at least one of $R_1$, $R_2$, $R_3$, and $R_4$ is i) and at least one of $R_1$, $R_2$, $R_3$, and $R_4$ is ii), where i) is a silicon bearing organic moiety having at least 2 carbons, and ii) is an organic moiety (II),

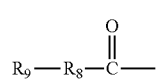

(II)

wherein $R_8$ is selected from a group consisting of $C_2$-$C_{10}$ alkylene, $C_3$-$C_{12}$ branched alkylene, $C_5$-$C_{12}$ cycloalkylene, $C_2$-$C_{10}$ alkylene containing a C=C double bond, $C_3$-$C_{12}$ branched alkylene containing a C=C double bond, and a $C_5$-$C_{12}$ cycloalkylene containing a C=C double bond, and $R_9$ is the alkyloxycarbonyl moiety (III), where $R_{10}$ is a $C_1$-$C_9$ alkyl group,

(III)

provided that the silicon bearing moiety bearing an organic moiety having at least 2 carbons i) ranges from about 10 mole % to about 80 mole %, and ii) ranges from about 20 mole % to about 90 mole % of the total groups $R_1$, $R_2$, $R_3$, and $R_4$.

2. The compound of claim 1, wherein the silicon bearing moiety bearing an organic moiety having at least 2 carbons i) ranges from 30 mole % to 60 mole %, and that the organic moiety ii) ranges from 30 mole % to 60 mole % of the total of groups $R_1$, $R_2$, $R_3$, and $R_4$.

3. The compound of claim 1, wherein in structure (I) at least one of $R_1$, $R_2$, $R_3$, and $R_4$ further comprises $C_1$-$C_8$ alkyl moiety ranging up to 50 mole % of the total of groups $R_1$, $R_2$, $R_3$, and $R_4$.

4. The compound of claim 1, wherein in structure (I) at least one of $R_1$, $R_2$, $R_3$, and $R_4$ further comprises $C_1$-$C_5$ alkyl moiety ranging up to 35 mole % of the total of groups $R_1$, $R_2$, $R_3$, and $R_4$.

5. The compound of claim 1, wherein the metal is selected from a group consisting of titanium, zirconium, tantalum, lead, antimony, thallium, indium, ytterbium, gallium, hafnium, aluminum, magnesium, molybdenum, germanium, tin, iron, cobalt, nickel, copper, zinc, gold, silver, cadmium, tungsten, and platinum.

6. The compound of claim 1, wherein the metal is more than one metal when n is 2 to 20.

7. The compound of claim 1 wherein the silicon bearing organic moiety having at least 2 carbon i) is selected from a group consisting of a trisubstitutedsilyl moiety (IV) and a siloxane moiety (V)

(IV)

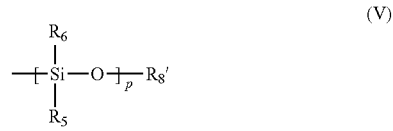

(V)

wherein $R_5$, and $R_6$, are independently selected from a group consisting of $C_1$-$C_8$ alkyl, $C_3$-$C_{12}$ branched alkyl, and aryl, $R_7$ is independently selected from a group consisting of $C_1$-$C_8$ alkyl, aryl and hydroxyl, and $R_8$' is selected from group consisting of hydrogen, a $C_1$-$C_8$ alkyl, a $C_1$-$C_8$ alkyl substituted with a hydroxyl group, a carboxylic acid group ($CO_2H$), and an aryl, and further where p represents the number of repeat units in the siloxane moiety (v).

8. The compound of claim 1, where the silicon bearing organic moiety having at least 2 carbon I) is a trisubstituted-silyl moiety (IV).

9. The compound of claim 1, where the silicon bearing organic moiety having at least 2 carbon I) is a siloxane moiety (V).

10. The compound of claim 1 where M is Ti, and the organic moiety i) is selected from the group consisting of

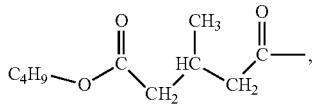

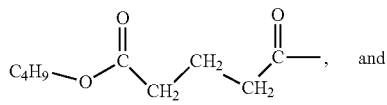, and

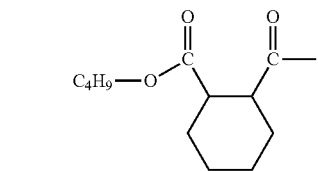

and further wherein n=4-16.

11. The compound of claim 1 where M is Ti and the silicon bearing organic moiety at least 2 carbon ii) is selected from the group consisting of

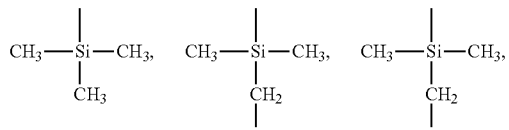

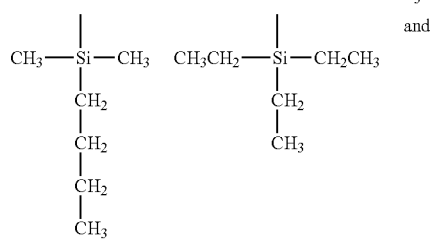

and

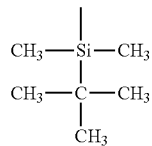

and further wherein n=4-16.

12. A composition comprising:
a. a soluble, multi-ligand-substituted metal compound of the following structure (I)

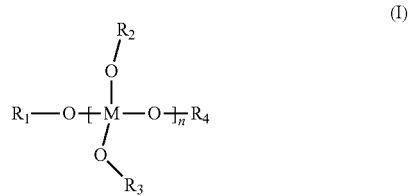

wherein M is a metal and n is 1 to 20, and wherein at least one of $R_1$, $R_2$, $R_3$, and $R_4$ is i) and at least at least one of $R_1$, $R_2$, $R_3$, and $R_4$ is ii), where i) is a silicon bearing organic moiety having at least 2 carbons, and ii) is an organic moiety (II),

wherein $R_8$ is selected from a group consisting of $C_2$-$C_{10}$ alkylene, $C_3$-$C_{12}$ branched alkylene, $C_5$-$C_{12}$ cycloalkylene, $C_2$-$C_{10}$ alkylene containing a C=C double bond, $C_3$-$C_{12}$ branched alkylene containing a C=C double bond, and a $C_5$-$C_{12}$ cycloalkylene containing a C=C double bond, and $R_9$ or the alkyloxycarbonyl moiety (III), where $R_{10}$ is a $C_1$-$C_8$ alkyl group,

provided that the silicon bearing moiety bearing an organic moiety having at least 2 carbons i) ranges from about 10 mole % to about 80 mole %, and ii) ranges from about 20 mole % to about 90 mole % of the total groups $R_1$, $R_2$, $R_3$, and $R_4$, and
(b) a solvent.

13. The composition of claim 12 where the composition further comprises a surfactant.

14. The composition of claim 12, further comprising at least one selected from a group consisting of a thermal acid generator, a thermal base generator, and a thermally activated peroxide.

15. The composition of claim 12, wherein n is 2 to 20.

16. The composition of claim 12, wherein n is 1.

17. The composition of claim 12, further comprising a crosslinking additive.

18. A method of manufacturing an electronic device on a substrate comprised of a patterned photoresist comprising, vias, trenches, holes or other hollow topographical features where the method comprises:
a. applying a composition from claim 12 onto the substrate;
b. baking the film;
c. removing the composition overlaying the top of the patterned photoresist; and
d. removing the resist with an oxygen plasma, thereby forming a negative tone image of the original patterned resist.

19. The method of claim 18, further comprising removing the residual composition with a stripper composition.

* * * * *